United States Patent
Schirmann et al.

[11] 3,978,049
[45] Aug. 31, 1976

[54] PROCESS FOR THE PREPARATION OF HYDRAZINE COMPOUNDS

[75] Inventors: Jean-Pierre Schirmann, Brignais; Pierre Tellier, Oullins; Henri Mathais, Meudon; Francis Weiss, Rethondes, all of France

[73] Assignee: Produits Chimiques Ugine Kuhlmann, Paris, France

[22] Filed: Jan. 16, 1974

[21] Appl. No.: 433,710

[30] Foreign Application Priority Data
Feb. 9, 1973  France .................. 73.04633

[52] U.S. Cl. .................. 260/240 G; 260/345.1; 260/566 B; 260/247.5 R; 260/293.87; 260/326.5 L; 260/326.86; 260/519; 260/345.9; 260/465 E; 260/518 R; 260/465.5 R; 260/558 H; 260/561 H; 260/397.6; 260/239.6
[51] Int. Cl.² ...................... C07C 109/00
[58] Field of Search .......... 260/566 B, 345.9, 345.1, 260/465 E, 465.5 R, 240 G, 247.5 R, 293.87, 326.5 L, 326.86, 239.6, 558 H, 561 H, 397.6, 519, 518 R

[56] References Cited
UNITED STATES PATENTS
2,870,206   1/1959   Meyer et al. .................. 260/566 B

*Primary Examiner*—Gerald A. Schwartz
*Attorney, Agent, or Firm*—Pennie & Edmonds

[57] ABSTRACT

This invention relates to a method for preparing an azine of the formula

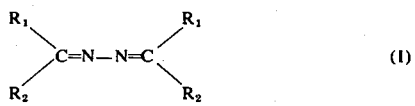

wherein $R_1$ and $R_2$, which may be the same or different, represent a hydrogen atom or a straight alkyl radical of from 1 to 12 carbon atoms, a branched alkyl or cycloalkyl radical of 3 to 12 carbon atoms, or a hydrocarbon radical of from 6 to 12 carbon atoms containing a benzene, naphthalene, or pyridine aromatic ring or $R_1$ and $R_2$ together form a straight or branched alkylene radical of 3 to 11 carbon atoms, one of which may be replaced by an oxygen atom, all of the above being unsubstituted or substituted with chlorine, bromine, or fluorine atoms, or ethylene, nitro, hydroxy, alkoxy, carboxylic or percarboxylic acid, amide, nitrile, or carboxylic ester groups, or a mixture of an azine of formula (I) and a hydrazone of the formula

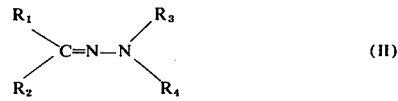

wherein $R_1$ and $R_2$ are as defined above and $R_3$ and $R_4$, which may be the same or different, represent a straight alkyl radical of from 1 to 12 carbon atoms, a branched alkyl or cycloalkyl radical of 3 to 12 carbon atoms, or a hydrocarbon radical of from 6 to 12 carbon atoms containing a benzene, naphthalene, or pyridine aromatic ring or $R_1$ and $R_2$ together form a straight or branched alkylene radical of 3 to 11 carbon atoms, one of which may be replaced by an oxygen atom, all of the above being unsubstituted or substituted by chlorine, bromine, fluorine, or iodine atoms, or hydroxy, ether oxide, carboxylic acid, carboxylic ester, nitrile, nitro, or sulphonic acid or amide groups or one of the two radicals $R_3$ and $R_4$ can represent a hydrogen atom, which comprises reacting hydrogen peroxide with ammonia or with a mixture of ammonia and primary or secondary amine of the formula

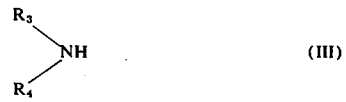

wherein $R_3$ and $R_4$ are as defined above, in the presence of a carbonyl compound of the formula

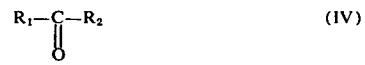

wherein $R_1$ and $R_2$ are as defined above, and a catalyst containing selenium.

5 Claims, No Drawings

PROCESS FOR THE PREPARATION OF HYDRAZINE COMPOUNDS

BACKGROUND OF THE INVENTION

I. Field of the Invention

This invention relates to the preparation of hydrazine compounds and specifically to the preparation of anazine or of a mixture of an azine and a hydrazone by reacting hydrogen peroxide with ammonia or with a mixture of ammonia and a primary or secondary amine in the presence of a carbonyl compound and a catalyst containing selenium.

II. Description of the Prior Art

It is known that the oxidation of carbonyl compounds, aldehydes and ketones in the presence of ammonia by mineral peroxide compounds leads to various compounds according to the nature of the peroxide compound and the conditions of operation. Thus the reaction between ammonia, an aldehyde or a ketone, and hydrogen peroxide leads to amino peroxides (see, for example, J. Chem. Soc. (c) 1969, page 2663) or to oximes in the presence of tungstic or molybdic acids (see, for example, J. Gen. Chem. U.S.S.R. 1960, 30, 1635).

It is also known that primary or secondary amines are easily oxidized by various peroxide compounds into widely differing oxygenated products such as the hydroxylamines, nitroso or nitro derivatives, oximes, compounds possessing azoxy structures, amides, etc., according to the particular structure of the reagents or the conditions of the reaction. For example, the oxidation of the aliphatic primary amines into nitroalkanes with peracetic acid (J. Am. Chem. Soc. 79, 5528, 1957) or other percarboxylic acids (see, for example, H.O. Larson in "The Chemistry of the Nitro and Nitroso Groups," part I, page 303, published by H. Feuer, Interscience, New York, 1969) has been described.

The aromatic primary amines have been oxidized into corresponding nitroso, nitro, or azoxy derivatives by pure percarboxylic acids or by a mixture of acetic acid and 30% aqueous solution of hydrogen peroxide (J. Am. Chem. Soc. 82 3454 (1960); see also W.H. Weaver in "The chemistry of the Nitro and Nitroso Groups" Part 2, page 29, published by H. Feuer, Interscience New York, 1970). Aniline has also been oxidized into azoxybenzene by hydrogen peroxide in the presence of acetonitrile (J. Org. Chem. 26, 659 (1961)).

In the previous patents and applications for patents the assignee of this application has moreover described new processes for the synthesis of azines (I) by oxidation of ammonia in the presence of a carbonyl compound (IV) with one of the peroxide compound mentioned above, in accordance with the general reaction $$2 \underset{R_2}{\overset{R_1}{\diagdown}}C = O + 2\ NH_3 + [O] \rightarrow \underset{R_2}{\overset{R_1}{\diagdown}}C = N - N = C\underset{R_2}{\overset{R_1}{\diagup}} + 3\ H_2O \quad (A)$$

The oxidation can be carried out with a percarboxylic acid (pending U.S. application Ser. No. 290,507, filed Sept. 20, 1972), a diacyl peroxide (pending U.S. application Ser. No. 308,836, filed Nov. 22, 1972), hydrogen peroxide in the presence of salts as catalysts (pending U.S. application Ser. No. 267,921, filed June 30, 1972), hydrogen peroxide in the presence of nitriles as co-reactants (French Pat. No. 2,092,734, 734, applied for June 12, 1970, and pending U.S. application Ser. No. 152,413, filed June 11, 1971), hydrogen peroxide in the presence of esters as co-reactants (pending U.S. application Ser. No. 340,763, filed Mar. 13, 1973), a hydrogen peroxide in the presence of amides or imides as co-reactants (pending U.S. application Ser. No. 341,057, filed Mar. 14, 1973), and hydrogen peroxide in the presence of cyanogen compounds as co-reactants (pending U.S. application Ser. No. 340,762, filed Mar. 13, 1973).

The applications have also described the synthesis of hydrazones (II) by the joint oxidation of a primary or secondary amine (III) and ammonia in the presence of a carbonyl compound (IV) with a percarboxylic acid, a diacyl peroxide, or hydrogen peroxide in the presence of salts or bases as catalysts or in the presence of co-reagents such as nitriles, esters, amides, imides, or cyanogen compounds (pending U.S. application Ser. No. 406,467 filed Oct. 15, 1973) in accordance with the general reaction $$\underset{R_2}{\overset{R_1}{\diagdown}}C = O + NH_3 + \underset{R_4}{\overset{R_3}{\diagdown}}NH + [O] \rightarrow \underset{R_2}{\overset{R_1}{\diagdown}}C = N - N\underset{R_4}{\overset{R_3}{\diagup}} + 2\ H_2O \quad (B)$$

SUMMARY OF THE INVENTION

This invention relates to the preparation of an azine (I) according to the general reaction (A) or of a mixture of an azine and a hydrazone (II) according to the general reaction (B), using as an oxidizing agent hydrogen peroxide in the presence of a catalyst containing selenium.

Broadly, the method of this invention is one of preparing an azine of the formula $$\underset{R_2}{\overset{R_1}{\diagdown}}C = N - N = C\underset{R_2}{\overset{R_1}{\diagup}} \quad (I)$$

wherein $R_1$ and $R_2$, which may be the same or different, represent a hydrogen atom or a straight alkyl radical of from 1 to 12 carbon atoms, a branched alkyl or cycloalkyl radical of 3 to 12 carbon atoms, or a hydrocarbon radical of from 6 to 12 carbon atoms containing a benzene, naphthalene, or pyridine aromatic ring or $R_1$ and $R_2$ together form a striaght or branched alkylene radical of 3 to 11 carbon atoms, one of which may be replaced by an oxygen atom, all of the above being unsubstituted or substituted with chlorine, bromine, or fluorine atoms or ethylene, nitro, hydroxy, alkoxy, carboxylic or percarboxylic acid, amide, nitrile, or carboxylic ester groups, or a mixture of an azine of formula (I) and a hydrazone of the formula $$\underset{R_2}{\overset{R_1}{\diagdown}}C = N - N\underset{R_4}{\overset{R_3}{\diagup}} \quad (II)$$

wherein $R_1$ and $R_2$ are as defined above and $R_3$ and $R_4$, which may be the same or different, represent a straight alkyl radical of from 1 to 12 carbon atoms, a branched alkyl or cycloalkyl radical of 3 to 12 carbon atoms, or a hydrocarbon radical of from 6 to 12 carbon atoms containing a benzene, naphthalene, or pyridine aromatic ring or $R_1$ and $R_2$ together form a straight or branched alkylene radical of 3 to 11 carbon atoms, one of which may be replaced by an oxygen atom, all of the above being unsubstituted or substituted by chlorine, bromine, fluorine, or iodine atoms, or hydroxy, ether oxide, carboxylic acid, amine, carboxylic ester, nitrile, nitro, or sulphonic acid or amide groups or one of the two radicals $R_3$ and $R_4$ can represent a hydrogen atom, which comprises reacting hydrogen peroxide with ammonia or with a mixture of ammonia and a primary or secondary amine of the formula

wherein $R_3$ and $R_4$ are as defined above, in the presence of a carbony compound of the formula

wherein $R_1$ and $R_2$ are as defined above, and a catalyst containing selenium.

DESCRIPTION OF THE PREFERRED EMBODIMENTS

It is known that selenium oxide is an effective agent for oxidizing aldehydes and ketones into alpha-dicarbonyl compounds. However, when hydrogen peroxide is reacted with ammonia or with a mixture of ammonia and a primary or secondary amine (III), and a carbonyl compound (IV) in the presence of selenium or an oxygen compound of selenium, one obtains an azine according to reaction (A) of a hydrazone according to reaction (B) accompanied by a variable quantity of azine (I), resulting from a reaction of the ammonia according to reaction (A).

If according to this process one reacts hydrogen peroxide with a mixture consisting solely of ammonia and a carbonyl compound (IV) in the presence of selenium or one of its oxygenated derivatives, one then obtains only the azine (I) according to the reaction (A).

Azines (I) and hydrazones (II), the joint production of which constitutes an other objective of the present invention, are useful synthesis agents which can in particular by hydrolyzed according to known methods so as to obtain the corresponding hydrazines or their salts with the liberation of the carbonyl compound which can be recycled.

Methods for converting the azines and hydrazones into hydrazines are set forth in U.S. Pat. Nos. 3,527,753 and 3,728,390.

The following are non-limitative examples of carbonyl compounds (IV) which can be used within the scope of the present invention:

aldehydes: formaldehyde, acetaldehyde, propionaldehyde, butyraldehyde, isobutyraldehyde, n-pentanal, pivalaldehyde, oenanthal, 2-ethyl-hexanal, Δ-3-tetrahydrobenzaldehyde, hexahydrobenzaldehyde, 5-norbornene-2-carboxaldehyde, tetrahydropyran-2-carboxaldehyde, benzaldehyde, monochlorobenzaldehydes, p-nitrobenzaldehyde, β-chloropropinonaldehyde, β-methoxy-propionaldehyde, 4-cyano-2,2-dimethyl-butyraldehyde;

ketones: acetone, 2-butanone, 2-pentanone, 3-pentanone, methyl isopropyl ketone, methylisobutylketone, ethylamylketone, methyl cyclohexylketone, acetophenone, benzophenone, cyclobutanone, cyclopentanone, cyclohexanone, 2-methyl-cyclohexanone, 3-methylcyclohexanone, 3,3,5-trimethyl-cyclohexanone, isophorone.

The following are non-limitative examples of amines (II) which can be used within the scope of the present invention: methylamine, dimethylamine, ethylamine, diethylamine, n-propylamine, isopropylamine, n-butylamine, di-n-butylamine, t-butylamine, the amylamines, cyclohexylamine, dicyclohexylamine, n-dodecylamine, monoethanolamine and diethanolamines, 2-methoxy-ethylamine, morpholine, pyrrolidine, piperidine, β-aminopropionitrile, β-aminopropionamide, aniline, the toluidines, mono and dichloro anilines or toluidines, bromoanilines, fluoroanilines, nitro and dinitroanilines and toluidines, o-, m- and p-anisidines, trifluoromethylanisidines, trifluormethylanilines, anthranilic acid, sulphanilic acid, diphenylamine, α-napthylamine, β-naphthylamine, the aminopyridines.

The catalyst may consist of metallic selenium or one of its mineral or organic oxygen compounds, Non-restrictive examples of the catalyst are selenium dioxide, selenious acid, the alkali and alkali earth selenites, selenium trioxide, selenic acid and alkali and alkali earth selenates. The quantity of catalyst used is generally 0.001 to 1 mole per moles of hydrogen peroxide used, and preferably advantageously between 0.01 and 0.1 moles per mole of hydrogen peroxide used. The catalyst may be entirely or partly soluble in the medium, or may become soluble during the course of the reaction.

The preferred mode of operation for preparing the azines and/or hydrazones according to the process of the invention consists of reacting the reagents in aqueous solution or in the presence of a solvent facilitating the homogenization of the mixture. This solvent is advantageously selected from among the alcohols or glycols, preferably aliphatic ones. Non-restrictive examples of solvents are methanol, ethanol, n-propanol, isopropanol, n-butanol, iso-butanol, t-butanol, secondary butanol, ethylene glycol, propyleneglycol, and diethyleneglycol.

The method of this invention may be used at atmospheric pressure or under a pressure which may range up to 10 atmospheres if necessary to maintain the ammonia in solution.

The reagents may be used in equimolecular quantities, but one may also use a deficit or a molar excess of one or more of the reagents. One may generally use 0.2 to 5 moles of aldehyde or of ketone and ammonia per mole of hydrogen peroxide, but it is advantageous to use from 2 to 4 moles. The reagents may be used in their usual commercial form. In particular, the hydrogen peroxide may be used in aqueous solutions containing 30 to 90% by weight of $H_2O_2$, and the ammonia may be used in ahydrous form or in the usual aqueous solution.

The reagents may be introduced simultaneously into the reaction medium or in any order, with a gradual rate of addition and at a temperature which permits effective control of the exothermicity of the reaction. One may also react the aldehyde or the ketone and the hydrogen peroxide in advance in a known manner and add the peroxide to the reaction. Likewise, one may react the aldehyde or the ketone and the ammonia separately before adding the hydrogen peroxide and the catalyst. Finally, one may prepare an amino peroxide in a known manner by reacting an aldehyde or a ketone with ammonia and hydrogen peroxide and then introduce the catalyst into the reaction medium.

It may be advantageous to add to the reaction medium known stabilizers for the hydrogen peroxide such as phosphoric acid, nitrilotriacetic acid, ethylenediamine tetracetic acid or their sodium salts.

The examples which follow illustrate the present invention without restricting it:

EXAMPLE 1

19.6 of cyclohexanone (0.2 moles), 16 g of an aqueous solution containing 21.2% by weight of ammonia (0.2 moles), 100 g of methanol, and 5 g of selenium oxide (0.045 moles) were placed in a reactor. This mixture was heated to 50°C, and 5 g of an aqueous solution containing 68.9% by weight of hydrogen peroxide (0.1 mole) were added during a 30 minutes period while gaseous ammonia was bubbled through the reaction mixture. The reaction was allowed to continue for 3 hours, and then the medium was determined by iodometry to contain 9.6 g of cyclohexanone azine (0.05 moles).

This solution was evaporated under a pressure of 200 mm Hg until the temperature reached 50°C. The residue was extracted with chloroform, and then the chloroform extract was dried over anhydrous sodium sulphate and distilled. 9 g of cyclohexanone azine (0.047 moles), which boiled at 87°–88°C under 0.2 mm Hg and crystallized when cooled (MP = 37°C), were obtained. This product had an infra-red spectrum which is identical with that described in the literature (Anal. Chem. 1964, 36, (7), 1349): characteristic band of the group >C=N- at 1640 cm$^{-1}$. Its ultra-violet spectrum, taken in solution in cyclohexane, showed a minimum at 216 m$\mu$ with a shoulder at 234 m$\mu$, and its nuclear magnetic resonance spectrum in deuterium chloroform at 60 megahertz showed two masses of peaks centered at S = 1.60 and 2.38 ppm, in the intensity ratio 3/2.

EXAMPLE 2

124 g of methanol, 16.6 g of acetone (0.28 moles), 16 g of 21.2% by weight aqueous ammonia solution (0.2 moles), and 5 g of selenium oxide (0.045 moles) were mixed in a reactor. This mixture was heated to 50°C, and 5 g of aqueous solution containing 68.9% by weight of hydrogen peroxide (0.1 moles) were added during a 30 minute period while ammonia was bubbled through the reaction mixture.

The reaction continued for 5 hours 30 minutes, and it was determined by iodometry that the reaction mixture contained 4 g of acetoneazine (0.036 moles), which was identified by its infra-red and nuclear magnetic resonance spectra. This corresponded to a yield of 36%, compared to the hydrogen peroxide used.

EXAMPLE 3

80 g of methanol, 15 g of acetone (0.26 moles), 16 g of 21.2% by weight aqueous ammonia solution (0.2 moles), 1 g of disodium salt of ethylene diaminetetracetic acid, and 1 g of selenium oxide (0.009 moles) were placed in a reactor. This mixture was heated to 50°C, and then 5 g of 68.9% by weight aqueous solution of hydrogen peroxide (0.1 moles) were added during a 30 minute period while gaseous ammonia was bubbled through the reaction medium. The reaction was allowed to continue for 8 hours, and the reaction mixture was then determined by iodometry to contain 5.3 g of acetoneazine (0.053 moles), which corresponds to a yield of 53%, compared to the hydrogen peroxide used.

EXAMPLE 4

Example 3 was repeated, but the acetone was replaced by 18.7 g (0.26 moles) of methylethylketone. The reaction proceeded for 4 hours, and the reaction mixture was determined by iodometry to contain 6.3 g of azine of methylethylketone (0.045 moles). This corresponds to a yield of 45%, compared to the hydrogen peroxide used.

EXAMPLE 5

Example 3 was repeated but the selenium oxide was replaced by 2 g of calcium selenite with 2 molecules of water of crystallization. After 3 hours of reaction, the reaction mixture was determined by iodometry to contain 0.67 g of the azine of acetone (0.006 moles). This corresponds to a yield of 6%, compared to the hydrogen peroxide used.

EXAMPLE 6

120 g of methanol, 22.6 g of acetone (0.39 moles), 18 g of a 21.2% by weight aqueous solution of ammonia, 1.5 g of selenium (0.019 moles) were placed in a reactor. This mixture was heated to 50°C, and 14.8 g of a 68.9% by weight aqueous solution of hydrogen peroxide (0.3 moles) were added during a period of half an hour while gaseous ammonia was bubbled through the reaction medium. After 3 hours of reaction, the reaction mixture was determined by iodometry to contain 0.56 g of acetoneazine (0.005 moles), which corresponds to a yield of 1.8%, compared to the hydrogen peroxide used.

EXAMPLE 7

120 g of methanol, 22.6 g of acetone (0.39 moles), 3 g of 21.2% by weight aqueous ammonia solution, 1.5 g of the disodium salt of ethylenediaminetetracetic acid, and 5 g of sodium selenite (0.029 moles) were placed in a reactor. This mixture was saturated with gaseous ammonia and heated to 50°C. 7.4 g of a 68.9% by weight aqueous solution of hydrogen peroxide (0.15 moles) were added during a period of 30 minutes while ammonia was bubled through. The reaction continued for 6 hours, and the reaction mixture was determined by iodometry to contain 8.7 g of acetoneazine (0.078 moles), which represents a yield of 52%, compared to the hydrogen peroxide used.

EXAMPLE 8

120 g of ethylene glycol, 22.6 g of acetone (0.39 moles), 3 g of 21.2% aqueous ammonia solution 1.5 g of disodium salt of ethylenediaminetetracetic acid, and 1.5 g of selenium oxide were placed in a reactor. This mixture was saturated with gaseous ammonia and then heated to 50°C. During a period of 30 minutes, 7.4 g of 68.9% by weight aqueous solution of hydrogen peroxide (0.15 moles) were added to the reaction mixture while ammonia was bubbled through. The reaction continued for 6 hours, and then the medium was determined to contain 7.85 g of acetoneazine (0.07 moles), which corresponds to a yield of 46%, compared to the hydrogen peroxide used.

EXAMPLE 9

120 g of methanol, 31.8 g of benzaldehyde (0.3 moles), 3 g of 21.2% by weight aqueous solution of ammonia, 1.5 g of the disodium salt of ethylenediaminetetracetic acid, and 1.5 g of selenium oxide (0.013 moles) were placed in a reactor. This mixture was saturated with gaseous ammonia. 7.4 g of 68.9% by weight aqueous solution of hydrogen peroxide (0.15 moles) were added at ambient temperature while ammonia was bubbled through the reaction medium. After a reaction period of 20 hours, the medium was determined to contain 1.25 g of benzaldazine (0.006 moles), which corresponds to a yield of 4%, compared to the hydrogen peroxide used.

EXAMPLE 10

Example 9 was repeated, but the benzaldehyde was replaced by isobutyraldehyde. The reaction was allowed to continue for 48 hours at ambient temperature, and the reaction mixture was determined to contain 0.98 g of the azine of isobutyraldehyde (0.007 moles), which corresponds to a yield of 4.6%, compared to the hydrogen peroxide used.

EXAMPLE 11

120 g of methanol, 22.6 g of acetone (0.39 moles), 9.3 g of aniline (0.1 moles), 3 g of a 22.1% by weight aqueous solution of ammonia, 1.5 g of the disodium salt of ethylenediaminetetracetic acid, and 1.5 g of selenium oxide (0.013 moles) were placed in a reactor. This mixture was saturated with gaseous ammonia and then heated to 50°C. 7.4 g of 68.9% by weight aqueous solution of hydrogen peroxide were added while gaseous ammonia was bubbled through the reaction mixture. After a reaction period of 6 hours, the mixture was determined by gas phase chromatography to contain 8.7 g of acetoneazine (0.078 moles) and 2.2 g of the phenyl hydrazone of acetone (0.015 moles).

EXAMPLE 12

A solution of 24.8 g of monomethylamine (0.8 moles), 13.6 g of ammonia (0.8 moles), 46.5 g of acetone (0.8 moles), 8 g of selenium oxide, 0.4 g of the disodium salt of ethylenediaminetetracetic acid in 128 g of methanol, and 60 g of water was prepared. 19.6 g of a 69.3% by weight aqueous solution of hydrogen peroxide (0.4 moles) were added during a period of 30 minutes while the temperature of the mixture was maintained at 30°C. The reaction was allowed to continue for 8 hours at the same temperature while ammonia was bubbled through the medium. 4 g of the methyl hydrazone of acetone (0.035 moles), which corresponds to a yield of 8.7%, compared to the hydrogen peroxide used, and 4.5 g of acetone azine (0.04 moles) were obtained.

The azines and hydrazones referred to in the above Examples were determined by gas phase chromotography, and the azine N—N groupings were determined by iodometry using the method of French Pat. No. 2,092,734, applied for June 12, 1970, and pending U.S. application Ser. No. 152,413, filed June 11, 1971, where a quantity of reaction mixture containing about 2 milliequivalents of hydrogen peroxide was withdrawn from the reactor and weighed; 12 cm$^3$ of aqueous sulphuric acid (30% by weight) and then 12 cm$^3$ of aqueous potassium iodide (30% by weight) were added to the mixture; after standing for 15 minutes in darkness, the released iodine was titrated by a decinormal solution of sodium tiosulphate; 50 cm$^3$ of a decinormal aqueous solution of iodine and then 30g of crystallized sodium acetate were added to adjust the pH of the sample to about 5; the sample was stirred and nitrogen evolved for about 2 minutes; and the excess iodine was titrated by a decinormal solution of sodium thiosulphate.

We claim:
1. A method of preparing an azine or a mixture of an azine and a hydrazone which comprises reacting a carbonyl compound selected from formaldehyde, acetaldehyde, propionaldehyde, butyraldehyde, isobutyraldehyde, n-pentanal, pivalaldehyde, oenanthal, 2-ethylhexanal, Δ-3-tetrahydrobenzaldehyde, hexahydrobenzaldehyde, 5-norbornene-2-carboxaldehyde, tetrahydropyran-2-carboxaldehyde, benzaldehyde, a monochlorobenzaldehyde, p-nitrobenzaldehyde, β-chloropropionaldehyde, β-methoxy-propionaldehyde, 4-cyano-2,2-dimethyl-butyraldehyde, acetone, 2-butanone, 2-pentanone, 3-pentanone, methylisopropyl ketone, methylcyclohexylketone, acetophenone, benzophenone, cyclobutanone, cyclopentanone, cyclohexanone, 2-methyl-cyclohexanone, 3-methylcyclohexanone, 3,3,5-trimethyl-cyclohexanone and isophorone, with ammonia or with ammonia and an amine, respectively, wherein the amine is selected from methylamine, dimethylamine, ethylamine, diethylamine, n-propylamine, isopropylamine, n-butylamine, di-n-butylamine, t-butylamine, an amylamine, cyclohexylamine, dicyclohexylamine, n-dodecylamine, mono and diethanolamines, 2-methoxyethylamine, morpholine, pyrrolidine, piperidine, β-aminopropionitrile, β-aminopropionamide, aniline, a toluidine, mono and dichloro anilines, mono and dichloro toluidines, a bromoaniline, a fluoroaniline, nitro and dinitroanilines, nitro and dinitrotoluidines, an anisidine, a trifluoromethylanisidine, a trifluoromethylaniline, anthranilic acid, sulphanilic acid, diphenylamine, a napthylamine, and an aminopyridine, in the presence of hydrogen peroxide and a catalytic amount of selenium or a compound of selenium selected from selenium dioxide, selenious acid, the alkali and alkali earth selenites, selenium trioxide, selenic acid, and alkali and alkali earth selenates.

2. A method of claim 1 where only ammonia is used as the amine and the product obtained is an azine.

3. A method of claim 1 where the reaction takes place in a solvent medium.

4. A method of claim 3 where the solvent used is a saturated alcohol having from 1 to 6 carbon atoms.

5. A method of claim 3 where the solvent used is a glycol having from 2 to 4 carbon atoms.

* * * * *

UNITED STATES PATENT AND TRADEMARK OFFICE
CERTIFICATE OF CORRECTION

PATENT NO. : 3,978,049
DATED : August 31, 1976
INVENTOR(S) : Jean-Pierre Schirmann et al.

It is certified that error appears in the above-identified patent and that said Letters Patent are hereby corrected as shown below:

Column 1, lines 7-8 "ana-zine" should be --an azine--

Column 1, line 49 "chemistry" should be --Chemistry--

Column 2, line 5 "2,092,734,734" should be --2,092,734--

Column 2, line 16 "applications" should be --applicants--

Column 2, lines 34-35 "mic-ture" should be --mixture--

Column 3, line 26 "carbony" should be --carbonyl--

Column 3, line 47 "...of a hydrazone" should be --or a hydrazone--

Column 4, line 15 "3-methylcyclohexanone" should be --3-methyl-cyclohexanone--

Signed and Sealed this

Sixteenth Day of November 1976

[SEAL]

Attest:

RUTH C. MASON
Attesting Officer

C. MARSHALL DANN
Commissioner of Patents and Trademarks